United States Patent
Carlson et al.

(10) Patent No.: US 6,770,677 B2
(45) Date of Patent: Aug. 3, 2004

(54) SYNERGISTIC MIXTURES OF BIS (TRICHLOROMETHYL) SULFONE AND 1,2-DIBROMO-2,4-DICYANOBUTANE

(75) Inventors: Paul E. Carlson, Pittsburgh, PA (US); H. Edwin Nehus, Pittsburgh, PA (US)

(73) Assignee: Verichem, Inc., Pittsburgh, PA (US)

( * ) Notice: Subject to any disclaimer, the term of this patent is extended or adjusted under 35 U.S.C. 154(b) by 0 days.

(21) Appl. No.: 10/357,063

(22) Filed: Feb. 3, 2003

(65) Prior Publication Data

US 2003/0156979 A1 Aug. 21, 2003

Related U.S. Application Data

(60) Provisional application No. 60/354,241, filed on Feb. 4, 2002.

(51) Int. Cl.$^7$ .......................... A01N 33/00; A01N 41/10; A61K 31/10
(52) U.S. Cl. .......................... 514/579; 514/709; 514/711
(58) Field of Search ................................ 514/579, 709, 514/711

(56) References Cited

U.S. PATENT DOCUMENTS

| 4,857,557 | A | | 8/1989 | Donofrio et al. |
| 5,266,218 | A | | 11/1993 | Roe et al. |
| 5,304,567 | A | | 4/1994 | Hsu |
| 5,312,841 | A | | 5/1994 | Paterson |
| 5,391,370 | A | | 2/1995 | Roe et al. |
| 5,416,122 | A | | 5/1995 | Donofrio et al. |
| 5,500,213 | A | | 3/1996 | Roe et al. |
| 5,658,467 | A | * | 8/1997 | LaZonby et al. ......... 2510/754 |
| 6,322,749 | B1 | * | 11/2001 | McCarthy et al. ............ 422/37 |

* cited by examiner

Primary Examiner—Alton N. Pryor
(74) Attorney, Agent, or Firm—William L. Krayer

(57) ABSTRACT

Combinations of Bis (Trichloromethyl) Sulfone and 1,2-dibromo-2, 4-dicyanobutane are shown to have synergistic antimicrobial properties. Preferred compositions use the two components in ratios of 1:99 to 99:1 by weight. The synergistic combinations are used in paints and adhesives, and in various industrial process waters. The synergistic compositions may be used together with a third microbiocide to enhance the composition's effectiveness against a wide variety of bacteria, molds, and yeasts and other microorganisms.

14 Claims, No Drawings

SYNERGISTIC MIXTURES OF BIS (TRICHLOROMETHYL) SULFONE AND 1,2-DIBROMO-2,4-DICYANOBUTANE

RELATED APPLICATION

This application claims the full benefit of provisional application No. 60/354,241 filed Feb. 4, 2002.

TECHNICAL FIELD

This invention relates to mixtures of two compounds synergistically effective as microbiocides. In particular, it relates to compositions comprising Bis (Trichloromethyl) Sulfone and 1,2-dibromo-2,4-dicyanobutane, and their use in industrial water processes and in other venues for combating microorganisms.

BACKGROUND OF THE INVENTION

Microbiological growth can cause contamination of products and spoilage of various products, resulting in a well known need for preservatives to prevent contamination. Preservatives are required for a broad range of products including but not limited to adhesives, cosmetics and toiletries, disinfectants and sanitizers, leather, metalworking fluids, paints and coatings, plastics and resins, latex polymers, textiles and wood. Failure to preserve these products adequately will result in spoilage and loss of the materials to be preserved and will result in an economic loss. Similarly, microbiological growths can have dire health and economic consequences if process waters are not adequately treated. Process waters include but are not limited to: industrial recirculating and cooling water, paper products and paper, petroleum production and leather tanning. Process waters are of concern because when fouled with biofilms that develop from the indigenous microbes present, biofilms may develop into thick gelatinous like masses. Slime is produced by a wide range of bacteria, fungi, and yeast. Slime will interfere with the process resulting in a loss of heat transfer, corrosion and fouling. Slime also detracts from systems cleanliness.

Bis (Trichloromethyl) Sulfone (sometimes referred to herein as "BTS") is used extensively as an antimicrobial agent in various industrial applications such as preservation of various materials including those listed above as well as to control unwanted microorganisms found in various process waters such as cooling water, paper mills and petroleum production. 1,2-dibromo-2,4-dicyanobutane is also a known biocide, used widely in various applications to combat microorganisms. We are not aware, however, of any disclosures that show combinations of the two materials to have synergistic effects.

SUMMARY OF THE INVENTION

This invention includes synergistic combinations of aqueous suspensions of Bis (Trichloromethyl) Sulfone with 1,2-dibromo-2,4-dicyanobutane, sometimes hereafter referred to as "DBDCB." The BTS and DBDCB may be mixed in preferred ratios that demonstrate synergistic antimicrobial effects. The blends are useful against a wide variety of Gram Positive and Gram-negative organisms.

Generally, we may use any ratio of BTS and DBDCB that demonstrates synergism against microorganisms. As a practical matter, combinations may be prepared in advance for sale or use in a wide spectrum of applications within the range of 1%–99% to 99%–1% by weight. We do not intend to be limited to these ratios, however. Other ratios may demonstrate synergistic effects to some degree, but we prefer to use the most efficient combinations. Our compositions may be used also together with other microbiocides to enhance effectiveness against a wide variety of bacteria, fungi and molds, in liquid products such as adhesives and paints, and in industrial process waters, including cooling water, paper mill process waters, petroleum industry process waters, and the like.

DETAILED DESCRIPTION OF THE INVENTION

BTS was found to produce synergistic blends with DBDCB. Synergism was demonstrated using a dose protocol. The actives were evaluated in synthetic white water with pH values of 5.5 and 8.0. The materials were tested against an artificial bacterial consortium containing approximately equal numbers of six bacterial strains. Although the test strains are representative of organisms present in paper mill systems, the effect is not limited to these bacteria. Two of the strains were *Kiebsiella pneumoia* (ATCC 13883) and *Pseudomonas aeruginosa* (ATCC 15442). The other four strains were isolated from papermill systems and have been identified as *Curtobacterium flaccumfaciens, Burkhlderia cepacia, Bacillus maroccanus,* and *Pseudomonas glethei.* Each strain was inoculated at 37° C. overnight, then suspended in sterile saline. Equal volumes of each strain were then combined to prepare the consortium. The bacterial consortium was distributed into the wells of a microliter plate in the presence or absence of various concentrations of the active materials. The microliter plates were incubated at 37° C. Optical density (O.D.) readings at 650 nm were taken initially ($t_0$) and after time 4 hours ($t_4$) of incubation.

The raw data was converted to "bacterial growth inhibition percentages" according to the following formula:

$$\% \text{ Inhibition} = [(a-b) \div a] \cdot 100$$

where:

$a$=(O.D. of control at $t_n$)−(O.D. of control at $t_0$)
$b$=(O.D. of treatment at $t_n$)−(O.D. of treatment at $t_0$)

The inhibition values can be plotted versus dosage for each active and the particular bland. This results in a dose response curve from which the dosage to yield 50% inhibition ($I_{50}$) can be calculated. In the examples (tables) below, the $I_{50}$ values are expressed as parts per million (ppm) of active material. The synergism index (SI) was calculated by the equations described by F. C. Kull, P. C. Eisman, H. D. Sylwestrowicz, and R. L. Mayer (1961), Applied Microbiology 9, 538–541. The values are based on the amount needed to achieve a specified end point. The end point selected for these studies was 50% inhibition of bacterial growth.

$$\text{Synergy Index}(SI) = (QA \div Qa) + (QB \div Qb)$$

where:

QA=quantity of compound A in mixture, producing the end point
Qa=quantity of compound $A_1$ acting alone, producing the end point
QB=quantity of compound B in mixture, producing the end point
Qb=quantity of compound $B_1$ acting alone, producing the end point If SI is less than 1, synergism exists; if SI is greater than 1, antagonism exists, if SI is equal to 1, an additive effect exists.

EXAMPLE 1

This example shows the synergistic activity of bis (Trichloromethyl) sulfone and 1,2-dibromo-2,4-dicyanobutane under a concurrent fed strategy, against an article bacterial consortium in synthetic white water at pH 5.5 and 8.0.

Sulfone & DBDCB* @ pH 5.5

| Sulfone (ppm) | DBDCB (ppm) | Ratio Sulfone:DBDCB | Synergy Index |
|---|---|---|---|
| 1.09 | 0.00 | 100 : 0 | 1.00 |
| 1.05 | 0.16 | 6.7 : 1.0 | 1.02 |
| 0.95 | 0.31 | 3.0 : 1.0 | 0.99* |
| 0.79 | 0.63 | 1.3 : 1.0 | 0.97* |
| 0.63 | 0.77 | 1.0 : 1.2 | 0.87* |
| 0.48 | 1.25 | 1.0 : 2.6 | 0.93* |
| 0.31 | 1.99 | 1.0 : 6.4 | 1.06 |
| 0.16 | 2.31 | 1.0 : 14.8 | 1.04 |
| 0.08 | 2.34 | 1.0 : 29.9 | 0.98* |
| 0.04 | 2.68 | 1.0 : 68.7 | 1.08 |
| 0.00 | 2.57 | 0 : 100 | 1.00 |
| 3.20 | 0.00 | 100 : 0 | 1.00 |
| 2.79 | 0.16 | 17.8 : 1.0 | 0.94* |
| 2.50 | 0.28 | 8.8 : 1.0 | 0.90* |
| 2.60 | 0.31 | 8.3 : 1.0 | 0.95* |
| 2.25 | 0.63 | 3.6 : 1.0 | 0.97* |
| 1.79 | 1.25 | 1.4 : 1.0 | 1.10 |
| 0.63 | 2.04 | 1.0 : 3.3 | 1.07 |
| 0.31 | 2.26 | 1.0 : 7.2 | 1.07 |
| 0.16 | 2.46 | 1.0 : 15.7 | 1.10 |
| 0.08 | 2.50 | 1.0 : 32.0 | 1.10 |
| 0.04 | 2.33 | 1.0 : 59.7 | 1.01 |
| 0.00 | 2.33 | 0 : 100 | 1.00 |

*DBDCB - 1,2-Dibromo-2,4-dicyanobutane (or 2-Bromo-2-bromomethylglutaronitril)

Synergy indices lower than unity are desirable, and are highlighted in rectangles imposed on the tables. All of the synergistic weight ratios are within the generally preferred range of 99:1 to 1:99. Based on these results, more preferred ranges may be chosen for different pH's. For example, at pH 5.5 (more generally, 4.5 to 6.5), a preferred range of TS:DBDCB is 1:5 to 4:1, and a more preferred range is 1:2 to 2:1. At pH 8.0 (more generally, 7.0 to 9.0), a preferred range of TS:DBDCB is 50:1 to 2:1 and a more preferred range is 30:1 to 10:1. Thus an overall preferred range for these pH's is 1:5 to 50:1, and a more preferred range is 1:2 to 30:1.

Our two-component synergistic composition may also be used with other compatible antimicrobial materials. These third components may be chosen from known microbiocides. In particular, they may be selected from the group consisting of 1,2-Benzisothiazolin-3-one;1,2-dibromo-2,4-dicyanobutane; 2,2-Dibromo-3-nitrilopropionamide; 2-Bromo-4-hydroxyacetophenone; B-Bromo nitrostyrene; Bis (1,4-bromacetoxy)-2-butene; Captan; 1-(3-chloroallyl)-3,5,7-triaza-1-azonia-adamantane; Dazomet; Dihalo-5,5-dimethyl hydantoins; Diodomethyl sulfone; Dipotassium ethylene bis (dithiocarbamate); Disodium ethylene bis (dithiocarbamate); Dithiol; Dodecylguanidine acetate; Dodecylguanidine HCl; Formaldehyde; Glutaraldehyde; Kathon; 2-Mercatobenzothiazole; Methylene bis Thiocyanate; N-[a-(nitroethylbenzyl] ethylenediamine; N-dialkyl methyl benzyl ammonium chloride; Potassium 2-mercaptobenzothiazole; Potassium Pentachlorophenate; Potassium Trichlorophenate; Sodium Mercaptobenzothiazole; Sodium Metam; Sodium Pentachlorophenate; Sodium Trichlorophenate; 2-(Thiocyanomethylthio) benzothiazole, and 1,3,5-Trimethylhexahydro-1,3,5-thiazine. One or more of these known microbiocides may be used with our synergistic composition(s) in weight ratios of 1:99 to 99:1 of the synergistic composition to the additional component(s) selected from the above group.

For use in industrial process water or as a preservative in adhesives and paints (which may be referred to herein as "products"), the synergistic compositions may be prepared as is known in the art in an aqueous carrier, suspension, solution, dispersion, or emulsion. Other additives known in the art may be used. While the concentrations in industrial process waters may vary with the conditions of the particular process water, effectiveness will not be guaranteed if the use concentrations are less than about 1 ppm BTS (with the DBDCB falling within the ratios described above) or less than 1 ppm DBDCB (with the BTS falling within the ratios described above).

We claim:

1. An antimicrobial composition comprising a synergistic mixture of Bis (Trichloromethyl) Sulfone and 1,2-dibromo-2,4-dicyanobutane wherein the ratio of Bis (Trichloromethyl) Sulfone to 1,2-dibromo-2,4-dicyanobutane is 1:5 to 50:1.

2. The antimicrobial composition of claim 1 wherein said ratio is 1:2 to 30:1.

3. The antimicrobial composition of claim 1 including as an additional component at least one microbiocide selected from the group consisting of 1,2-Benzisothiazolin-3-one; 1,2-dibromo-2,4-dicyanobutane; 2,2-Dibromo-3-nitrilopropionamide; 2-Bromo-4-hydroxyacetophenone; B-Bromo nitrostyrene; Bis (1,4-bromacetoxy)-2-butene; Captan; 1-(3-chloroallyl)-3,5,7-triaza-1-azonia-adamantane; Dazomet; Dihalo-5, 5-dimethyl hydantoins; Diodomethyl sulfone; Dipotassium ethylene bis (dithlocarbamate); Disodium ethylene bis (dithiocarbamate); Dithiol; Dodecylguanidine acetate; Dodecylguanidine HCl; Formaldehyde; Glutaraldehyde; Kathon; 2-Mercatobenzothiazole; Methylene bis Thiocyanate; N-[a-(nitroethylbenzyl] ethylenediamine; N-dialkyl methyl benzyl ammonium chloride; Potassium 2-mercaptobenzothiazole; Potassium Pentachlorophenate; Potassium Trichlorophenate; Sodium Mercaptobenzothiazole; Sodium Metam; Sodium Pentachlorophenate; Sodium Trichlorophenate; 2-(Thiocyanomethylthio) benzothiazole, and 1,3,5-Trimethylhexahydro-1,3,5-thiazine.

4. A product including a composition of claim 1.

5. A product of claim 4 wherein said product is an adhesive.

6. A product of claim 4 wherein said product is paint.

7. Method of combating microorganisms in an industrial process water comprising adding thereto an antimicrobial composition comprising a synergistic mixture of Bis (Trichloromethyl) Sulfone and 1,2-dibromo-2,4-dicyanobutane.

8. Method of claim 7 wherein said ratio is 1:2 to 30:1.

9. Method of claim 7 wherein said antimicrobial composition includes an additional component selected from the group consisting of 1,2-Benzisothiazolin-3-one; 1,2-dibromo-2,4-dicyanobutane; 2,2-Dibromo-3-nitrilopropionamide; 2-Bromo-4-hydroxyacetophenone; B-Bromo nitrostyrene; Bis (1,4-bromacetoxy)-2-butene; Captan; 1-(3-chloroallyl)-3,5,7-triaza-1-azoniaadamantane; Dazomet; Dihalo-5,5-dimethyl hydantoins; Diodomethyl sulfone; Dipotassium ethylene bis (dithiocarbamate); Disodium ethylene bis (dithiocarbamate); Dithiol; Dodecylguanidine acetate; Dodecylguanidine HCl; Formaldehyde; Glutaraldehyde; Kathon; 2-Mercatobenzothiazole; Methylene bis Thiocyanate; N-[a-(nitroethylbenzyl] ethylenediamine; N-dialkyl methyl benzyl ammonium chloride; Potassium 2-mercaptobenzothiazole; Potassium Pentachlorophenate; Potassium Trichlorophenate; Sodium Mercaptobenzothiazole; Sodium Metam; Sodium Pentachlorophenate; Sodium Trichlorophenate; 2-(Thiocyanomethylthio) benzothiazole, and 1,3,5-Trimethylhexahydro-1,3,5-thiazine.

10. Method of claim 7 wherein said industrial process water has a pH of 4.5 to 6.5 and said synergistic mixture has a weight ratio of Bis(Trichloromethyl) Sulfone to 1,2-dibromo-2,4-dicyanobutane of 1:5 to 4:1.

11. Method of claim 7 wherein said industrial process water has a pH of 7.0 to 9.0 and said synergistic mixture has a weight ratio of Bis(Trichloromethyl) Sulfone to 1,2-dibromo-2,4-dicyanobutane of 50:1 to 2:1.

12. Method of claim 7 wherein said industrial process water is an industrial cooling water.

13. Method of claim 7 wherein said industrial process water is a paper mill process water.

14. Method of claim 7 wherein said industrial process water is a petroleum industry process water.

* * * * *